United States Patent [19]
Villa et al.

[11] Patent Number: 5,817,861
[45] Date of Patent: Oct. 6, 1998

[54] PROCESS FOR THE PREPARATION OF AN INTERMEDIATE USEFUL IN THE SYNTHESIS OF IODINATED CONTRAST MEDIA

[75] Inventors: Marco Villa, Milan; Antonio Nardi, Paderno Dugnano; Maurizio Paiocchi, Milan, all of Italy

[73] Assignee: Bracco International BV, Amsterdam, Netherlands

[21] Appl. No.: 822,463

[22] Filed: Mar. 21, 1997

[30] Foreign Application Priority Data

Mar. 29, 1996 [IT] Italy .................................. MI96A0621

[51] Int. Cl.$^6$ .................................................. C07C 229/04
[52] U.S. Cl. ......................... 560/39; 424/9.454; 562/41; 562/43; 564/142; 564/153
[58] Field of Search ..................................... 564/153, 142; 424/9.454; 560/39, 41, 43

[56] References Cited

U.S. PATENT DOCUMENTS 5,412,149  5/1995  Kuhnt et al. ............................... 560/35

FOREIGN PATENT DOCUMENTS

MI 92
A002451  of 1992  Italy .
1472050  4/1977  United Kingdom .
WO 92/14539  of 1992  WIPO .

OTHER PUBLICATIONS

Italian Pamacopia Monograph form the "Iopamidolum", 1994.

Primary Examiner—Shailendra Kumar
Attorney, Agent, or Firm—Stevens, Davis, Miller & Mosher, L.L.P.

[57] ABSTRACT

A process for the preparation of (S)-N,N'-bis[2-hydroxy-1-(hydroxymethyl)ethyl]-5-(2-acetoxy-propionylamino)-2,4,6-triiodo-isophthalamide, an intermediate useful for the synthesis of iopamidol, by reaction between L-5-(2-acetoxy-propionylamino)-2,4,6-triiodoisophthaloyl dichloride and 2-amino-1,3-propanediol in N-methylpyrrolidone and in the presence of a base, is described.

7 Claims, No Drawings

PROCESS FOR THE PREPARATION OF AN INTERMEDIATE USEFUL IN THE SYNTHESIS OF IODINATED CONTRAST MEDIA

The present invention relates to a process for the preparation of an intermediate useful in the synthesis of iodinated contrast media and, more particularly, it relates to a process for the preparation of the compound (S)-N,N'-bis[2-hydroxy-(1-hydroxymethyl)ethyl]-5-(2-acetoxy-propionylamino)-2,4,6-triiodo-isophthalamide (from now on indicated as compound A).

Compound A, described in the British patent No. 1,472,050 (Savac AG), is an intermediate for the synthesis of (S)-N,N'-bis[2-hydroxy-(1-hydroxymethyl)ethyl]-5-(2hydroxy-propionylamino)-2,4,6-triiodo-isophthalamide, a non-ionic X-rays contrast medium better known with its International Non-proprietary Name iopamidol.

To our knowledge, the industrial synthesis of compound A still follows the synthetic scheme described in the British patent No. 1,472,050 and, in particular, it consists of the following steps:

1. preparation of 5-amino-2,4,6-triiodo-isophthalic acid by iodination of 5-aminoisophthalic acid;
2. preparation of 5-amino-2,4,6-triiodo-isophthaloyl dichloride;
3. reaction of 5-amino-2,4,6-triiodo-isophthaloyl dichloride with L-2-acetoxy-propionyl chloride to afford L-5-(2-acetoxy-propionylamino)-2,4,6-triiodo-isophthaloyl dichloride (compound B);
4. reaction of compound B with 2-amino-1,3-propanediol (serinol) in dimethylacetamide and in the presence of a base to afford compound A.

There were described alternative synthetic pathways which comprise, for instance, the inversion in the order of steps 3 and 4, namely the reaction of 5-amino-2,4,6-triiodo-isophthaloyl dichloride with serinol at first and the subsequent reaction of the resultant N,N'-bis[2-hydroxy-1-(hydroxymethyl)ethyl]-5-amino-2,4,6-triiodo-isophthalamide with L-2-acetoxy-propionyl chloride to afford compound A, but to the extent of our knowledge they were not industrially applied. The reaction of step 4 was described in example 1a of the aforementioned British patent.

Such a reaction is carried out by adding a solution of serinol in dimethylacetamide (DMA) to a solution of L-5-(2-acetoxy-propionylamino)-2,4,6-triiodo-isophthaloyl dichloride and tributylamine in DMA.

The ratio among L-5-(2-acetoxy-propionylamino)-2,4,6-triiodo-isophthaloyl dichloride (compound B), serinol and the base (tributylamine) is, in equivalents, 1:2.5:2. The reaction is carried out at 50° C. and furnishes, after a few hours, the desired product with a 92% yield.

The same reaction can be analogously carried out by using more than 4 equivalents of serinol so that serinol acts also as a base acceptor of hydrochloric acid in place of tributylamine (International patent application WO 92/14539—Bracco S.p.A./Tecnofarmaci S.p.A.).

As it clearly appears also from the aforementioned International patent application the crude product obtained from the reaction between compound B and serinol in DMA as a solvent with or without the presence of a different base such as tributylamine, has a very low purity because it contains relevant quantities of the hydrochloride of the used base (tributylamine or serinol hydrochloride) and reaction by-products difficult to separate because structurally very close to compound A and to iopamidol. Substantially the same profile of impurities is present in the crude iopamidol, which is generally obtained through hydrolysis directly from crude compound A.

The problem of the purity of iopamidol, as well as of all the iodinated contrast media, is extremely important because, just for its function as a diagnostic medium, the product must be pharmacologically inert. Moreover, the pharmacological inertness must be achieved for the normally used doses, namely for doses even equal to several grams. For these reasons, the Italian Pharmacopea (FU IX) requires that iopamidol has a content of impurities lower than 0.25%.

The impurities described in the monography on iopamidol (Pharmeuropa Vol.6, No. 4, December 1994, pages 343–345) are seven and one of these is represented by N-[2hydroxy -(1-hydroxymethyl)ethyl]-N'-dimethyl-5-(2-hydroxy-propionylamino)-2,4,6triiodo-isophthalamide (from now on indicated as impurity I), whose presence is very likely due to the release of dimethylamine from DMA.

It is clear that the substitution of DMA with another solvent which does not release dimethylamine should lead to the elimination of impurity I.

The technical problem to be solved however is not represented by the mere elimination of impurity I by substituting DMA, but by the use of a solvent different from DMA which enables to afford the product at least with analogous yields, with an improved impurity profile and without the formation of other impurities.

To this extent, our attempts to use dimethylformamide, methylene chloride or dimethoxyethane as a solvent resulted to be negative at all. The reaction in fact did not afford the desired product or afforded it with extremely low yields and in admixture with high amounts of by-products.

Satisfactory results in terms of yields and of total purity were achieved by using acetone or a lower alcohol as solvents, as described in the Italian patent application No. MI92A002451 in the name of the present Applicant.

Nevertheless, even by maintaining an acceptable degree of purity, the obtained iopamidol contained other impurities in place of impurity I.

Now we have surprisingly found that by substituting DMA with N-methylpyrrolidone (NMP) the formation of impurity I is completely eliminated while maintaining substantially unchanged the profile of the other impurities, with a consequent significant increase in the total purity of the resultant compound A and of iopamidol.

Therefore, object of the present invention is a process for the preparation of(S)-N,N'-bis[2-hydroxy-1-(hydroxymethyl)ethyl]-5-(2-acetoxy-propionylamino)-2,4,6-triiodo-isophthalamide by reaction between L-5-(2-acetoxy-propionylamino)-2,4,6-triiodo-isophthaloyl dichloride and 2-amino-1,3-propanediol in a solvent and in the presence of a base characterized in that the solvent is N-methylpyrrolidone.

N-methylpyrrolidone is a solvent of normal industrial use.

The use of N-methylpyrrolidone allows to achieve several advantages with respect to the use of DMA described in the literature.

From a practical point of view the yields are substantially equivalent and the reaction can be carried out also at room temperature.

Impurity I is not formed and contemporaneously no new impurity, due to the use of N-methylpyrrolidone as a solvent, is formed in compound A or in iopamidol.

It is evident that this provides a significant reduction of the total impurities present in iopamidol with a remarkable industrial advantage.

The base used in the process object of the present invention can be an organic base such as an amine.

The amine is preferably used in molar excess with respect to compound B, more preferably in a molar ratio from 2.1 to 2.5 with respect to compound B.

Examples of usable amines are tributylamine and serinol, according to what reported in the literature for the reaction with DMA, or other amines more advantageous from an economical and industrial point of view such as triethylamine.

When triethylamine is used as a base, it is more convenient to use a triethylamine purified by treatment with acyl chlorides. The purification can be carried out also in situ by adding small amounts of acyl chloride in the reaction system according to known methods (Organic Solvents, III Ed., Riddick & Bunger, pages 825–826).

Besides the aforementioned advantages, the use of N-methylpyrrolidone as a solvent in the reaction between L-5-(2-acetoxy-propionylamino)-2,4,6-triiodo-isophthaloyl dichloride and 2-amino-1,3-propanediol allows to use also an inorganic base in place of the amine.

This latter characteristic aspect of the present invention is of extreme importance because the usable base can be a much more economic and advantageous base from an industrial point of view such as, for instance, sodium carbonate.

It is evident in fact how the use of an inorganic base, such as sodium carbonate, provides a further significant advantage with respect to known methods.

In fact, by using an organic base as a hydrochloric acid acceptor, this remains in remarkable amounts in the reaction crude (in the form of hydrochloride) and must be necessarily eliminated.

When the base is serinol, it is necessary not only to eliminate it as an impurity from the reaction crude or from iopamidol but also to recover it because it is a high costing reagent.

Therefore a preferred embodiment of the process object of the present invention is the use of an inorganic base such as an alkali metal carbonate.

The inorganic base is preferably sodium carbonate and it is generally used in a slight excess with respect to the equivalents of L-5-(2-acetoxy-propionylamino)-2,4,6-triiodo-isophthaloyl dichloride.

As already pointed out, the use of sodium carbonate is advantageous from an industrial point of view because it is a low costing reagent, which does not require recovery and which is very easily removable during the normal work-up of the reaction crude. Preferably, the subsequent hydrolysis and purification can be carried out according to the method described in the British patent No. 2287024 in the name of the present Applicant.

Moreover, also when inorganic bases are used in the process object of the present invention, the impurity profile is not modified and iopamidol maintains the high degree of purity characteristic of the use of N-methylpyrrolidone as a solvent according to what above reported.

The chance of substituting the amines with inorganic bases is still more surprising because by using DMA as a solvent, the reaction between L-5-(2-acetoxy-propionylamino)-2,4,6-triiodo-isophthaloyl dichloride and serinol in the presence of sodium carbonate yields compound A with an unacceptable impurity profile for the high content of impurities.

A practical embodiment of the process object of the present invention is the following. Compound B is added to a solution of purified triethylamine and serinol in N-methylpyrrolidone, keeping the mixture at room temperature for a few hours.

After cooling the reaction mixture and dilution with water, the solution is directly passed through a serie of columns respectively packed with a strong cationic resin, with a weak anionic resin, a strong anionic resin and a further weak anionic resin, to desalt and hydrolyze compound A and to remove the by-products of the hydrolysis reaction from crude iopamidol.

The thus obtained high purity iopamidol is then crystallized, preferably from sec.butanol.

A preferred practical embodiment of the process object of the present invention is the following.

Compound B and sodium carbonate are added to a solution of serinol in N-methylpyrrolidone then keeping the reaction mixture at room temperature for a few hours.

After dilution with water and cooling the reaction mixture, the solution is acidified, degassed and passed through a serie of columns respectively packed with a strong cationic resin, with a weak anionic resin, a strong anionic resin and further with a weak anionic resin to desalt and hydrolyze compound A and to remove the by-products of the hydrolysis reaction from crude iopamidol.

The thus obtained high purity iopamidol is then crystallized, preferably from sec.butanol.

With the aim of better illustrating the present invention the following examples are now given.

EXAMPLE 1

Preparation of Compound A with N-methylpyrrolidone and Serinol

N-methylpyrrolidone (34 g) and serinol (12.4 g; 136.2 mmoles) were loaded into a 250 ml round flask, equipped with mechanical stirring and kept under nitrogen.

The solution was cooled with an ice and water bath at 7° C. and L-5-(2-acetoxy-propionylamino)-2,4,6-triiodo-isophthaloyl dichloride (22.2 g; 31.2 mmoles) was added portionwise in 60 minutes keeping the temperature between 8° and 12° C.

The reaction mixture was then kept under stirring at 25° C. for 16 hours, cooled at 8°–10° C. and then water (68 g) was added in about 30 minutes keeping the temperature below 15° C.

The solution was filtered on celite to remove eventual insoluble particles and the filter was washed with water (10 g).

The resultant solution was passed through a column packed with IMAC HP111E (55 ml).

The eluate was adsorbed on a column packed with IMAC HP 661 (90 ml).

The eluate was adsorbed on a column packed with IMAC HP 551 (180 ml).

The addition of water through the three columns was continued till all the N-methylpyrrolidone was eluted from the bottom of the column packed with IMAC HP 551. To complete the hydrolysis of compound A to iopamidol, water kept at 35° C. was passed through the column IMAC HP 551 for 1 hour.

After interrupting it for 1 hour, the flux of water was continued for a further hour at 35° C. and for 10 minutes at 20° C.

Acetic acid at 5% was then added (203 g).

The eluate was passed through a column containing IMAC HP 661 (90 ml).

Terminated the acetic acid, the addition of water was continued collecting fractions containing iopamidol which were collected together and concentrated under vacuum (20 mmHg, 70° C. bath).

The residue was crystallized from sec.butanol (90 g) furnishing, after drying at 50° C. under vacuum, pure iopamidol (20 g) which resulted to be devoid of traces of the impurity I by HPLC analysis.

Sum of the impurities<0.25% (HPLC).

EXAMPLE 2

Preparation of Compound A with N-methylpyrrolidone and Triethylamine

Purified triethylamine (15.7 g; 155.3 mmoles) was loaded into a 500 ml round flask, equipped with mechanical stirring and kept under nitrogen.

The mixture was kept under stirring for 2 hours at 25° C. and N-methylpyrrolidone (80 g) and serinol (14.2 g; 156.1 mmoles) were added.

The solution was cooled with an ice and water bath at 7° C. and L-5-(2-acetoxy-propionylamino)-2,4,6-triiodo-isophthaloyl dichloride (50 g; 70.4 mmoles) was added portionwise in 60 minutes keeping the temperature between 8° and 12° C.

The reaction mixture was then kept under stirring at 25° C. for 16 hours, cooled at 8–10° C. and then water (186 g) was added in about 30 minutes keeping the temperature below 15° C.

The solution was filtered on celite to remove eventual insoluble particles and the filter was washed with water (20 g).

The resultant solution was passed through a column packed with IMAC HP111E (110 ml).

The eluate was adsorbed on a column packed with IMAC HP 661 (180 ml).

The eluate was adsorbed on a column packed with IMAC HP 551 (360 ml).

The addition of water through the three columns was continued till all the N-methylpyrrolidone was eluted from the bottom of the column packed with IMAC HP 551. To complete the hydrolysis of compound A to iopamidol, water kept at 35° C. was passed through the column IMAC HP 551 for 1 hour.

After interrupting it for 1 hour, the flux of water was continued for a further hour at 35° C. and for 10 minutes at 20° C.

Acetic acid at 5% was then added (465 g).

The eluate was passed through a column containing IMAC HP 661 (180 ml).

Terminated the acetic acid, the addition of water was continued collecting fractions containing iopamidol which were collected together and concentrated under vacuum (20 mmHg, 70° C. bath).

The residue was crystallized from sec.butanol (190 g) furnishing, after drying at 50° C. under vacuum, pure iopamidol (44.8 g) which resulted to be devoid of traces of the impurity I by HPLC analysis.

Sum of the impurities<0.25% (HPLC).

EXAMPLE 3

Preparation of Compound A with N-methylpyrrolidone and Sodium Carbonate

N-methylpyrrolidone (40 g), serinol (7.1 g; 78.1 mmoles) and sodium carbonate (5.6 g; 52.8 mmoles) were loaded into a 250 ml round flask, equipped with mechanical stirring and kept under nitrogen.

The solution was cooled with an ice and water bath at 7° C. and L-5-(2-acetoxy-propionylamino)-2,4,6-triiodo-isophthaloyl dichloride (25 g; 35.2 mmoles) was added portionwise in 60 minutes keeping the temperature between 8° and 12° C.

The reaction mixture was then kept under stirring at 25° C. for 16 hours, cooled at 8–10° C. and then water (93 g) was added in about 30 minutes keeping the temperature below 15° C.

Hydrochloric acid 1N was added to bring the pH to a value comprised between 5 and 5.5 and the solution was kept under stirring at reduced pressure (30 mmHg) for 30 minutes.

The solution was filtered on celite to remove eventual insoluble particles and the filter was washed with water (10 g).

The resultant solution was passed through a column packed with IMAC HP111E (55 ml).

The eluate was adsorbed on a column packed with IMAC HP 661 (90 ml).

The eluate was adsorbed on a column packed with IMAC HP 551 (180 ml).

The addition of water through the three columns was continued till all the N-methylpyrrolidone was eluted from the bottom of the column packed with IMAC HP 551. To complete the hydrolysis of compound A to iopamidol, water kept at 35° C. was passed through the column IMAC HP 551 for 1 hour.

After interrupting it for 1 hour, the flux of water was continued for a further hour at 35° C. and for 10 minutes at 20° C.

Acetic acid at 5% was then added (235 g).

The eluate was passed through a column containing IMAC HP 661 (90 ml).

Terminated the acetic acid, the addition of water was continued collecting fractions containing iopamidol which were collected together and concentrated under vacuum (20 mmHg, 70° C. bath).

The residue was crystallized from sec.butanol (95 g) furnishing, after drying at 50° C. under vacuum, pure iopamidol (22.1 g) which resulted to be devoid of traces of the impurity I by HPLC analysis.

Sum of the impurities<0.25% (HPLC).

EXAMPLE 4

Preparation of Compound A with N-methylpyrrolidone and Triethylamine

Purified triethylamine (8.3 g; 82.2 mmoles) was loaded into a 250 ml reactor, equipped with mechanical stirring and kept under nitrogen.

The mixture was kept under stirring for 2 hours at 25° C. and N-methylpyrrolidone (40 g) and serinol (7.2 g; 79.1 mmoles) were added.

L-5-(2-acetoxy-propionylamino)-2,4,6-triiodo-isophthaloyl dichloride (25 g; 35.2 mmoles) was added portionwise in 60 minutes keeping the temperature between 25° and 30C by means of a water jacket.

The reaction mixture was then kept under stirring at 50° C. for 5 hours, cooled at 8–10° C. and then water (93 g) was added in about 30 minutes keeping the temperature below 15° C.

The solution was filtered on celite to remove eventual insoluble particles and the filter was washed with water (10 g).

The resultant solution was passed through a column packed with IMAC HP111E (55 ml).

The eluate was adsorbed on a column packed with IMAC HP 661 (90 ml).

The eluate was adsorbed on a column packed with IMAC HP 551 (180 ml).

The addition of water through the three columns was continued till all the N-methylpyrrolidone was eluate from the bottom of the column packed with IMAC HP 551. To complete the hydrolysis of compound A to iopamidol, water kept at 35° C. was passed through the column IMAC HP 551 for 1 hour.

After interrupting it for 1 hour, the flux of water was continued for a further hour at 35° C. and for 10 minutes at 20° C.

Acetic acid at 5% was then added (235 g).

The eluate was passed through a column containing IMAC HP 661 (90 ml).

Terminated the acetic acid, the addition of water was continued collecting fractions containing iopamidol which were collected together and concentrated under vacuum (20 mmHg, 70° C. bath).

The residue was crystallized from sec.butanol (95 g) furnishing, after drying at 50° C. under vacuum, pure iopamidol (22 g) which resulted to be devoid of traces of the impurity I by HPLC analysis.

Sum of the impurities<0.25% (HPLC).

EXAMPLE 5

Preparation of Compound A with N-methylpyrrolidone and Sodium Carbonate

N-methylpyrrolidone (40 g), serinol (7.2 g; 79.1 mmoles) and sodium carbonate (5.6 g; 52.8 mmoles) were loaded into a 250 ml reactor, equipped with mechanical stirring and kept under nitrogen.

L-5-(2-Acetoxy-propionylamino)-2,4,6-triiodo-isophthaloyl dichloride (25 g; 35.2 mmoles) was added portionwise in 60 minutes keeping the temperature between 25° and 30° C. by means of a water jacket.

The reaction mixture was then kept under stirring at 50° C. for 5 hours, cooled at 8–10° C. and then water (93 g) was added in about 30 minutes keeping the temperature below 15° C.

Hydrochloric acid 1N was added to bring the pH to a value comprised between 5 and 5.5 and the solution was kept under stirring at reduced pressure (30 mmHg) for 30 minutes.

The solution was filtered on celite to remove eventual insoluble particles and the filter was washed with water (10 g).

The resultant solution was passed through a column packed with IMAC HP111E (55 ml).

The eluate was adsorbed on a column packed with IMAC HP 661 (90 ml).

The eluate was adsorbed on a column packed with IMAC HP 551 (180 ml).

The addition of water through the three columns was continued till all the N-methylpyrrolidone was eluted from the bottom of the column packed with IMAC HP 551. To complete the hydrolysis of compound A to iopamidol, water kept at 35° C. was passed through the column IMAC HP 551 for 1 hour.

After interrupting it for 1 hour, the flux of water was continued for a further hour at 35° C. and for 10 minutes at 20° C.

Acetic acid at 5% was then added (235 g).

The eluate was passed through a column containing IMAC HP 661 (90 ml).

Terminated the acetic acid, the addition of water was continued collecting fractions containing iopamidol which were collected together and concentrated under vacuum (20 mmHg, 70° C. bath).

The residue was crystallized from sec.butanol (95 g) furnishing, after drying at 50° C. under vacuum, pure iopamidol (22.1 g) which resulted to be devoid of traces of the impurity I by HPLC analysis.

Sum of the impurities<0.25% (HPLC).

COMPARATIVE EXAMPLE 6

Preparation of Compound A with Dimethylformamide and Serinol

Dimethylformamide (40 g) and serinol (14 g; 154 mmoles) were loaded into a 250 ml round flask, equipped with mechanical stirring and kept under nitrogen.

The solution was cooled with an ice and water bath at 7° C. and L-5-(2-acetoxy-propionylamino)-2,4,6-triiodo-isophthaloyl dichloride (25 g; 35.2 mmoles) was added portionwise in 60 minutes keeping the temperature between 8° and 12° C.

The reaction mixture was then kept under stirring at 25° C. for 16 hours, cooled at 8–10° C. and then water (93 g) was added in about 30 minutes keeping the temperature below 15° C.

The solution was treated following the procedure described in the preceding examples 1–5.

The resultant residue was crystallized from sec.butanol furnishing, after drying at 50° C. under vacuum, iopamidol (22 g) which resulted to contain an amount of impurity I higher than 0.5% (HPLC analysis).

COMPARATIVE EXAMPLE 7

Preparation of Compound A with Dimethylacetainide and Triethylamine

Purified triethylamine (6.8 g; 67.2 mmoles), dimethylacetamide (32 g) and serinol (6.2 g; 68.1 mmols) were loaded into a 250 ml round flask, equipped with mechanical stirring and kept under nitrogen, at 25° C.

The solution was cooled with an ice and water bath at 7° C. and L-5-(2-acetoxy-propionylamino)-2,4,6-triiodo-isophthaloyl dichloride (20 g; 28.1 mmoles) was added portionwise in 60 minutes keeping the temperature between 8° and 12° C.

The reaction mixture was then kept under stirring at 25° C. for 16 hours, cooled at 8–10° C. and then water (74.4 g) was added in about 30 minutes keeping the temperature below 15° C.

The solution was treated following the procedure described in the preceding examples 1–5.

The residue was crystallized from sec.butanol furnishing, after drying at 50° C. under vacuum, iopamidol (17.8 g) which resulted to contain 0.08% of impurity I by HPLC analysis.

What we claim is:

1. A process for the preparation of (S)-N,N'-bis[2-hydroxy-1-(hydroxymethyl)ethyl]-5-(2-acetoxy-propionylamino)-2,4,6-triiodo-isophthalamide by reaction between L-5(2-acetoxy-propionylamino)-2,4,6-triiodo-isophthaloyl dichloride and 2-amino-1,3-propanediol in a solvent and in the presence of a base characterized in that the solvent is N-methylpyrrolidone.

2. A process according to claim 1 wherein the base is an amine.

3. A process according to claim 2 wherein the amine is selected among tributylamine, serinol and triethylamine.

4. A process according to claim 3 wherein the amine is triethylamine.

5. A process according to claim 1 wherein the base is an alkali metal carbonate.

6. A process according to claim 5 wherein the base is sodium carbonate.

7. A process for the preparation of (S)-N,N'-bis[2-hydroxy-1-(hydroxymethyl)ethyl]-5-(2-hydroxypropionylamino)-2,4,6-triiodo-isophthalamide which comprises the preparation of (S)-N,N'-bis[2-hydroxy-1-(hydroxymethyl)ethyl]-5-(2-acetoxy-propion-ylamino)-2,4,6-triiodo-isophthalamide with the process according to claim 1.

* * * * *